US012220442B2

(12) United States Patent
Cao et al.

(10) Patent No.: US 12,220,442 B2
(45) Date of Patent: Feb. 11, 2025

(54) ANTIEPILEPTIC TOXIN MARTENTOXIN AND USE THEREOF

(71) Applicant: Shanghai Institute of Organic Chemistry, Chinese Academy of Sciences, Shanghai (CN)

(72) Inventors: Chunyang Cao, Shanghai (CN); Yonghua Ji, Shanghai (CN); Xinlian Liu, Shanghai (CN); Jie Tao, Shanghai (CN); Shuzhang Zhang, Shanghai (CN); Chunxi Wang, Shanghai (CN)

(73) Assignee: Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 774 days.

(21) Appl. No.: 17/291,016

(22) PCT Filed: Nov. 5, 2019

(86) PCT No.: PCT/CN2019/115704
§ 371 (c)(1),
(2) Date: May 4, 2021

(87) PCT Pub. No.: WO2020/094002
PCT Pub. Date: May 14, 2020

(65) Prior Publication Data
US 2022/0040260 A1    Feb. 10, 2022

(30) Foreign Application Priority Data

Nov. 5, 2018 (CN) .......................... 201811307810.6

(51) Int. Cl.
| | | |
|---|---|---|
| *A61K 38/17* | (2006.01) | |
| *A61K 38/00* | (2006.01) | |
| *A61K 45/06* | (2006.01) | |
| *A61P 25/08* | (2006.01) | |

(52) U.S. Cl.
CPC .......... *A61K 38/1767* (2013.01); *A61K 45/06* (2013.01); *A61P 25/08* (2018.01)

(58) Field of Classification Search
CPC .... A61K 38/1767; A61K 38/00; A61K 38/17; A61K 45/06; A61P 25/08
See application file for complete search history.

(56) References Cited

U.S. PATENT DOCUMENTS

| | | | |
|---|---|---|---|
| 7,803,769 B2 | 9/2010 | Sullivan et al. | |
| 7,820,623 B2 | 10/2010 | Sullivan et al. | |
| 7,825,093 B2* | 11/2010 | Sullivan ................. | A61K 47/60 530/324 |
| 7,833,979 B2* | 11/2010 | Sullivan ................. | A61P 29/00 530/300 |
| 2007/0071764 A1* | 3/2007 | Sullivan .................... | A61P 9/00 530/391.1 |
| 2008/0160121 A1* | 7/2008 | Donovan ........... | A61K 38/4893 424/780 |
| 2009/0318341 A1* | 12/2009 | Sullivan .................. | A61P 37/00 514/4.8 |
| 2020/0352978 A1* | 11/2020 | Van Battum ......... | A61K 31/713 |

FOREIGN PATENT DOCUMENTS

| | | |
|---|---|---|
| CN | 1344745 A | 4/2002 |
| CN | 101232903 A | 7/2008 |
| CN | 101564530 A | 10/2009 |
| CN | 109106943 A | 1/2019 |
| WO | WO-2006/116156 A2 | 11/2006 |

OTHER PUBLICATIONS

Goldenberg MM, "Overview of Drugs Used for Epilepsy and Seizures," Pharmacy and Therapeutics, Jul. 2010, 392-415. (Year: 2010).*
Yampolsky et al., "The Exchangeability of Amino Acids in Proteins," Genetics, 2005, 170: 1459-1472. (Year: 2005).*
Rudinger, J., "Characteristics of the amino acids as components of a peptide hormone sequence," Peptide Hormones, J.A. Parsons, MA, BM, BCh, Jun. 1976, pp. 1-7. (Year: 1976).*
Berendsen, HJC, "A Glimpse of the Holy Grail?" Science, 1998, 282: 642-643. (Year: 1998).*
Ngo et al., "Computational Complexity, Protein Structure Prediction, and the Levinthal Paradox," The Protein Folding Problem and Tertiary Structure Prediction, K. Merc, Jr. and S. Le Grand Editors, 1994, 494-495. (Year: 1994).*
Schinzel et al., "The phosphate recognition site of *Escherichia coli* Maltodextrin phosphorylase," 1991, 286 (1,2): 125-128. (Year: 1991).*
Sigma, "Designing Custom Peptides," pp. 1-2. Accessed Dec. 6, 2004. (Year: 2004).*
Voet et Voet, Biochemistry, Second Edition, John Wiley & Sons, Inc., pp. 235-241. (Year: 1995).*
Bradley et al., "Limits of Cooperativity in a Structurally Modula Protein: Response of the Notch Ankyrin Domain to Analogous Alanine Substitutions in Each Repeat," J. Mol. Biol., 2002, 324: 373-386. (Year: 2002).*
Shi et al., "Inhibition of Martentoxin on Neuronal BK Channel Subtype ($\alpha$+$\beta$4): Implications for a Novel Interaction Model," Biophysical Journal, vol. 94, pp. 3706-3713, 2008.
Search Report issued Apr. 21, 2020, in Chinese Patent Application No. 2018113078106.
Tao, Jie, et al., "Martentoxin: A unique ligand of BK channels," *Acta Physiologica Sinica*, Aug. 25, 2012, 64(4): 355-364.

(Continued)

*Primary Examiner* — Julie Ha
(74) *Attorney, Agent, or Firm* — Banner & Witcoff, Ltd.

(57) ABSTRACT

Anti-epileptic toxin Martentoxin (MarTX), derivatives thereof, and uses thereof are described. Specifically, the use of Martentoxin or an active fragment thereof or a pharmaceutically acceptable salt thereof in preparing a preparation or composition for treating and/or preventing epilepsy is described. It has been confirmed for the first time that the Martentoxin can effectively treat and/or prevent epileptic symptoms.

14 Claims, 7 Drawing Sheets
Specification includes a Sequence Listing.

(56) References Cited

OTHER PUBLICATIONS

Tao Jie, "Anticonvulsant effect of martentoxin and molecular mechanism of its recognition on BK channels," *China doctoral dissertation database, Medical and health science and technology*, May 2014.

Tao, Jie, et al., "Recombinant Expression and Functional Characterization of Martentoxin: A Selective Inhibitor for BK Channel ($\alpha+\beta$)," *Toxins* 2014, 6, 1419-1433.

Wang, Jun, et al., "Martentoxin, a large-conductance $Ca^{2+}$-activated $K^+$ channel inhibitor, attenuated TNF-$\alpha$-induced nitric oxide release by human umbilical vein endothelial cells," The Journal of Biomedical Research, 2013, 27(5): 386-393.

\* cited by examiner

ANTIEPILEPTIC TOXIN MARTENTOXIN AND USE THEREOF

CROSS REFERENCE TO RELATED APPLICATIONS

This application is the National Stage of International Application No. PCT/JP2019/115704, filed Nov. 5, 2019, and claims benefit of Chinese Patent Application No. 201811307810.6 filed on Nov. 5, 2018, the full contents of all of which are hereby incorporated by reference in their entirety.

REFERENCE TO A SEQUENCE LISTING

The instant application contains a sequence listing which has been submitted in ASCII format via EFS-Web and is hereby incorporated by reference in its entirety. Said ASCII copy, created on May 3, 2021 is named 522200-0001-U.S. Pat. No. 2-SL.txt and is 6,865 bytes in size.

TECHNICAL FIELD

The present invention relates to the field of polypeptide drug, specifically to an antiepileptic toxin Martentoxin and the use thereof.

BACKGROUND OF THE INVENTION

Epilepsy is a chronic disease that leads to transient brain dysfunction chronic diseases, characterized by recurrent seizures caused by sudden abnormal discharge of brain neurons. It is estimated that there are about 400,000 new patients with epilepsy every year. Epilepsy has become the second most common disease after headache in neurology department in China.

The pathogenesis of epilepsy is very complex, but it is generally believed that the imbalance between excitation and inhibition of central nervous system will lead to epilepsy.

Based on the different initial locations and transmission modes of abnormal discharges, the pathogenic factors of epilepsy can be divided into abnormal ion channel function, abnormal neurotransmitters, abnormal neuroglia cells and other different factors.

Ion channel is one of the bases of tissue excitability regulation in vivo. Studies have shown that sodium ion channel, potassium ion channel, calcium ion channel and other channels are related to epilepsy.

In view of the diverse pathogenesis of epilepsy, researchers have developed various antiepileptic drugs with different mechanisms of action and different targets. Small molecule drugs such as phenytoin sodium and carbamazepine can selectively act on voltage-dependent sodium channels to block the rapid release of sodium-dependent action potentials, and achieve anticonvulsant effect. Trimethadione is a selective T-type calcium ion channel blocker, which inhibits hyperexcitability of neurons. Perampanel is an AMPA-type glutamate receptor (α-amino-3-hydroxy-5-methyl-4-isoxazolpropionic acid receptor, which mediates rapid excitatory synaptic transmission in the central nervous system) antagonist. It can prevent and treat epilepsy by inhibiting the glutamate activity of postsynaptic AMPA receptor and reducing hyperexcitability of neurons.

However, the effect of current epileptic drugs is still unsatisfactory. For example, most small molecule drugs have great side effects after long-term administration. In addition, the causes of epilepsy are diverse, so the current small molecule drugs are difficult to apply to tailor-made treatment.

Therefore, there is an urgent need in the field to develop new drugs with high specificity and/or minimal side effects for the prevention and/or treatment of epilepsy.

SUMMARY OF THE INVENTION

The purpose of the invention is to provide a drug with high specificity and/or minimal side effects for the prevention and/or treatment of epilepsy and uses thereof.

In a first aspect of the invention, it provides a use of a MarTX toxin or an active fragment thereof, or a pharmaceutically acceptable salt thereof, in the manufacture of a formulation or composition for the treatment and/or prevention of epilepsy.

In another preferred embodiment, the epilepsy comprises epilepsy caused by increased excitability of cerebral cortex (or epilepsy caused by abnormal excitation of neurons).

In another preferred embodiment, the epilepsy is characterized by increased activity of large-conductance calcium- and voltage-activated potassium channels, resulting in increased excitability of the cerebral cortex.

In another preferred embodiment, the epilepsy comprises epilepsies of human and non-human mammals (such as rodents).

In another preferred embodiment, the epilepsy comprises PTZ-induced epilepsy, especially PTZ-induced epilepsy in rats.

In another preferred embodiment, the MarTX toxin comprises recombinant, synthetic or natural MarTX polypeptides.

In another preferred embodiment, the MarTX toxin comprises wild-type and mutant MarTX toxins.

In another preferred embodiment, the MarTX toxin comprises the amino acid sequence of SEQ ID NO: 2.

In another preferred embodiment, the MarTX toxin comprises recombinant protein labeled with one or more protein tags at the N or C terminus of the sequence of SEQ ID NO: 2 within the range of maintaining protein activity.

In another preferred embodiment, the protein tag is selected from the group consisting of an MBP tag, a His tag, a GST tag, an SUMO tag, a TRX tag, an HA tag, a Flag tag, and combinations thereof.

In another preferred embodiment, the MarTX toxin comprises the amino acid sequence obtained by substitution, deletion, alteration, insertion, or addition of one or more amino acids based on the sequence SEQ ID NO: 2 within the range of maintaining protein activity.

In another preferred embodiment, the MarTX toxin comprises insertion of one or more amino acids at the N terminus or C terminus of the sequence SEQ ID NO: 2, within the range of maintaining protein activity, and the number of inserted amino acid residues comprises 1 to 10, preferably 1 to 5, more preferably 1 to 3.

In another preferred embodiment, the MarTX toxin is recombinant.

In another preferred embodiment, the MarTX toxin is recombinantly expressed in *Escherichia coli*.

In another preferred embodiment, the amino acid sequence of the MarTX toxin is shown as SEQ ID No.: 3.

In another preferred embodiment, the composition is a pharmaceutical composition.

In another preferred example, the pharmaceutical composition comprises a pharmaceutically acceptable carrier and (a) MarTX toxin or an active fragment thereof.

In another preferred embodiment, the ingredient (a) accounts for 0.1-99.9 wt %, preferably 10-99.9 wt %, more preferably 70%-99.9 wt % of the pharmaceutical composition, based on the total weight.

In another preferred embodiment, the pharmaceutical composition is liquid, solid, or semi-solid.

In another preferred embodiment, the dosage form of the pharmaceutical composition is an injection or a topical dosage form.

In another preferred embodiment, the dosage form of the pharmaceutical composition comprises an injection or a lyophilized formulation.

In another preferred embodiment, the composition is a liquid composition.

In another preferred embodiment, the carrier is selected from the group consisting of infusion carrier and/or injection carrier, preferably one or more carriers selected from the group consisting of normal saline, glucose saline, and combinations thereof.

In another preferred embodiment, the composition or formulation may be administered alone or in combination.

In another preferred embodiment, the combination administration comprises administration in combination with other therapeutic agents for the treatment and/or prevention of epilepsy.

In another preferred embodiment, the other therapeutic agent is selected from the group consisting of:

carbamazepine, fluoropyridine, gabapentin, lamotrigine, oxcarbazepine, phenytoin, phenytoin sodium, retigabine, topiramate, sodium 2-propylpentanoate, ethosuximide, sodium valproate, and combinations thereof.

In another preferred embodiment, the dosage form of the pharmaceutical composition is an injection form.

In another preferred embodiment, the pharmaceutical composition is administered intravenously, subcutaneously, intramuscularly or intracranially.

In another preferred embodiment, the injection is administered by microinfusion pumps.

In another preferred embodiment, the injection is administered by intracranial administration, preferably by intracerebroventricular (ICV) delivery into a subject.

In another preferred embodiment, the injection is administered to the ipsilateral hippocampus of a subject.

In another preferred embodiment, the subject comprises mammals.

In another preferred embodiment, the mammal comprises human or non-human mammals.

In another preferred embodiment, the non-human mammal comprises rodent (such as rat, mice), primate (such as monkey).

In a second aspect of the invention, it provides a composition product, wherein the composition product comprises:

(i) a first pharmaceutical composition comprising a first active ingredient (a) MarTX toxin or an active fragment thereof and a pharmaceutically acceptable carrier;

(ii) a second pharmaceutical composition comprising a second active ingredient (b) another drug for the treatment and/or prevention of epilepsy and a pharmaceutically acceptable carrier.

In another preferred embodiment, the first pharmaceutical composition and the second pharmaceutical composition are the same composition.

In another preferred embodiment, the pharmaceutical composition product comprises:

(a) a first active ingredient, wherein the first active ingredient is MarTX toxin or an active fragment thereof;

(b) a second active ingredient, wherein the second active ingredient is another or additional pharmaceutical active ingredient for the treatment and/or prevention of epilepsy;

(c) a pharmaceutically acceptable carrier.

In another preferred embodiment, the first pharmaceutical composition and the second pharmaceutical composition are different compositions.

In another preferred embodiment, the content of ingredient (a) is 0.1-99.9 wt %, preferably 10-99.9 wt %, more preferably 70%-99.9 wt %.

In another preferred embodiment, the other or additional pharmaceutical active ingredient for the treatment and/or prevention of epilepsy comprises:

carbamazepine, fluoropyridine, gabapentin, lamotrigine, oxcarbazepine, phenytoin, phenytoin sodium, retigabine, topiramate, sodium 2-propylpentanoate, ethosuximide, sodium valproate, and combinations thereof.

In a third aspect of the present invention, it provides a kit and the kit comprises:

(i) a first container, and a first pharmaceutical composition located in the first container, wherein the first pharmaceutical composition comprises a first active ingredient (a) MarTX toxin or an active fragment thereof and a pharmaceutically acceptable carrier;

(ii) a second container, and a second pharmaceutical composition located in the second container, wherein the second pharmaceutical composition comprises a second active ingredient (b) another drug for the treatment and/or prevention of epilepsy and a pharmaceutically acceptable carrier.

In another preferred embodiment, the kit further comprises (ii) instructions.

In another preferred embodiment, the active ingredient (b) comprises: carbamazepine, fluoropyridine, gabapentin, lamotrigine, oxcarbazepine, phenytoin, phenytoin sodium, retigabine, topiramate, sodium 2-propylpentanoate, ethosuximide, sodium valproate, and combinations thereof.

In another preferred embodiment, the first container and the second container are the same or different containers.

In another preferred embodiment, the drug in the first container is a prescribed preparation containing MarTX toxin or an active fragment thereof.

In another preferred embodiment, the drug in the second container is a prescribed preparation containing a drug for the treatment and/or prevention of epilepsy.

In another preferred embodiment, the instructions comprise instructions for the treatment and/or prevention of epilepsy by administering the active ingredient (a) and optionally (b).

In another preferred embodiment, the instructions describe the active ingredient (a) and optionally (b) in dosage forms as injections.

In another preferred embodiment, the injection is injected into a subject by intracerebroventricular (ICV) delivery.

It should be understood that in the present invention, any of the technical features specifically described above and below (such as in the Example) can be combined with each other, thereby constituting new or preferred technical solutions which will not redundantly be described one by one herein.

(A, B) represent the saline control group and the MarTX toxin experimental group injected into the ipsilateral hippocampus, respectively. (A1, B1) represent the CA1 region, (A2, B2) represent the CA3 region, and (A3, B3) represent the DG region. (C) represents c-Fos histogram of the ipsilateral hippocampus injected. Compared with saline group *p<0.05, p<0.01, *p<0.001 (one-way ANOVA).

Figure 3:
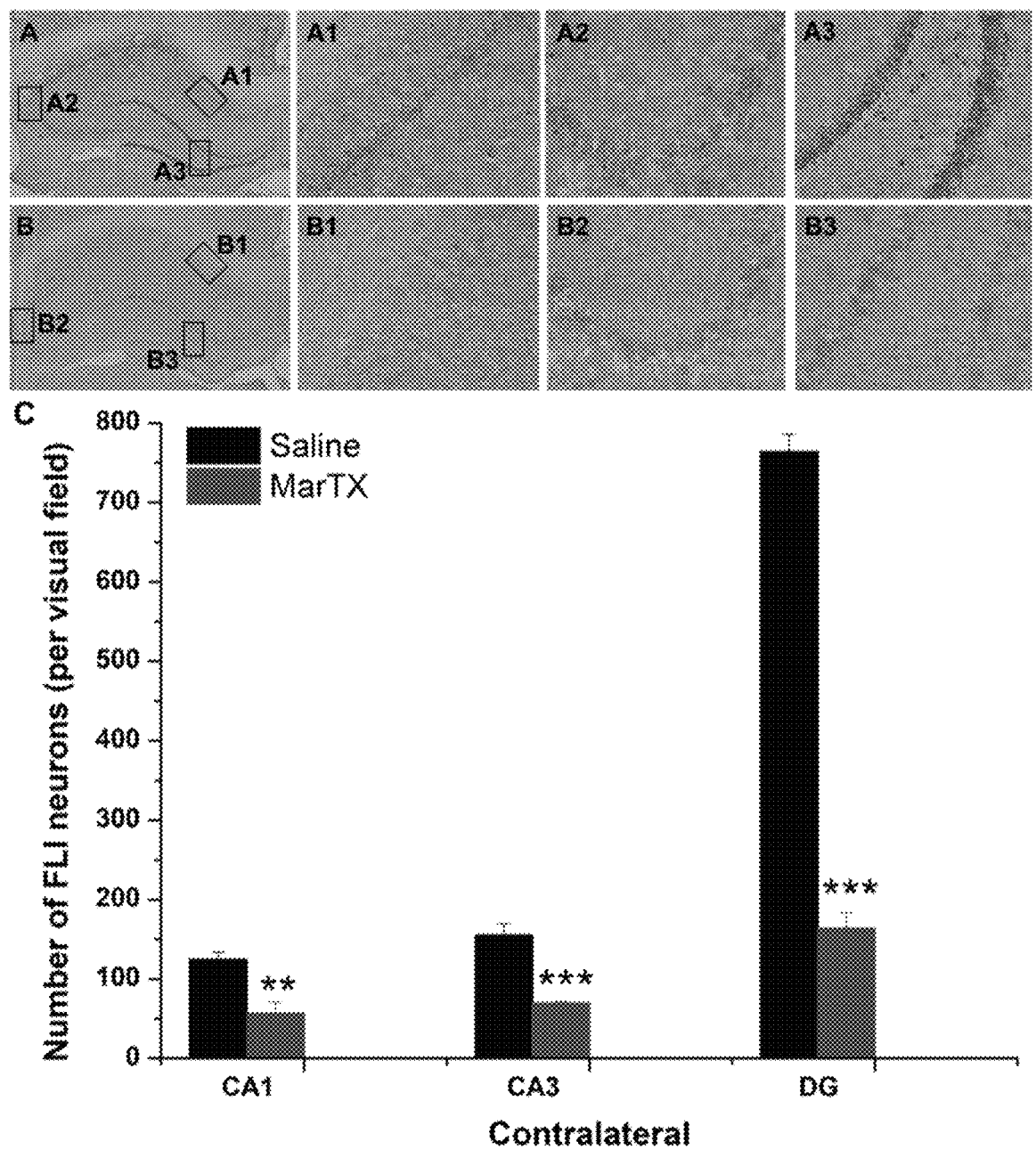

FIG. 3 shows the inhibitory effect of MarTX toxin on c-Fos expression induced by PTZ injection in contralateral hippocampus.

(A, B) represent the saline control group and the MarTX toxin experimental group injected into the contralateral hippocampus, respectively. (A1, B1) represent the CA1 region, (A2, B2) represent the CA3 region, and (A3, B3) represent the DG region. (C) represents c-Fos histogram of the contralateral hippocampus injected. Compared with saline group *p<0.05, p<0.01, *p<0.001 (one-way ANOVA).

Figure 4:
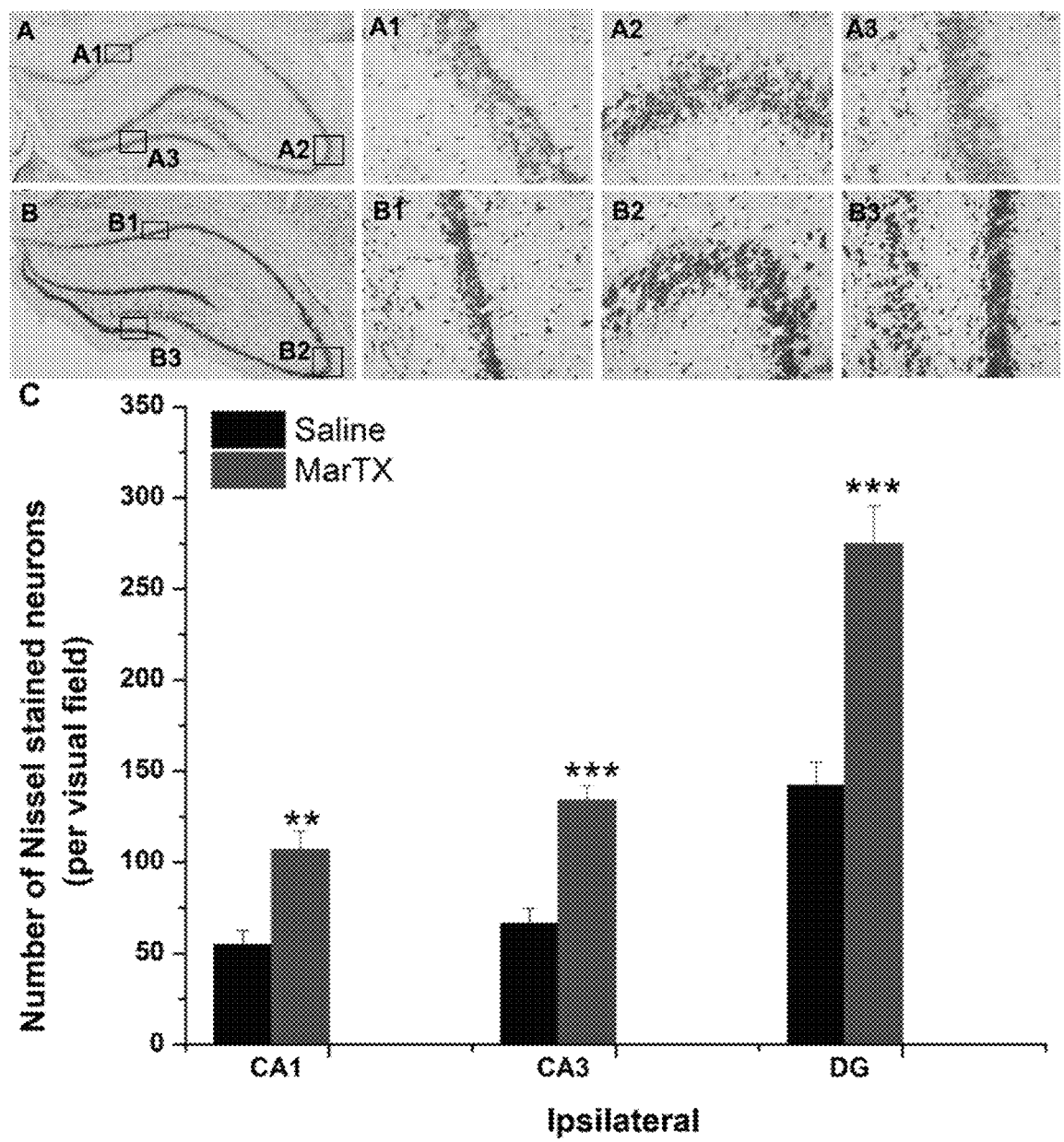

FIG. 4 shows the effect of MarTX toxin injected on PTZ-induced ipsilateral hippocampal neurons.

(A, B) represent the saline control group and the MarTX toxin experimental group injected into the ipsilateral hippocampus, respectively. (A1, B1) represent the CA1 region, (A2, B2) represent the CA3 region, and (A3, B3) represent the DG region. (C) represents statistical graph of the number of nissel body staining neurons of the ipsilateral hippocampus injected. Compared with saline group *p<0.05, p<0.01, *p<0.001 (one-way ANOVA).

Figure 5:
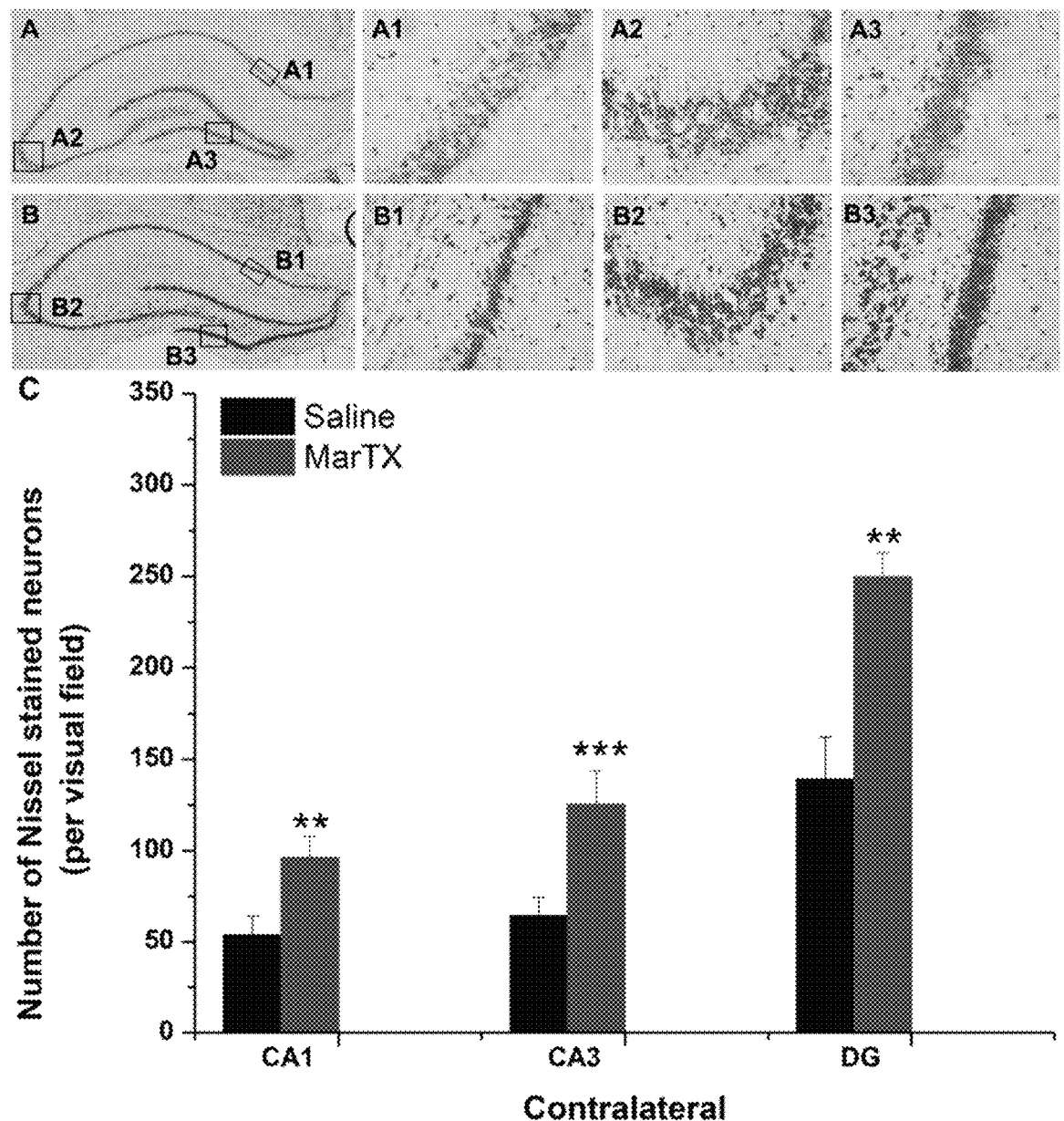

FIG. 5 shows the effect of MarTX toxin injected on PTZ-induced contralateral hippocampal neurons.

(A, B) represent the saline control group and the MarTX toxin experimental group injected into the contralateral hippocampus, respectively. (A1, B1) represent the CA1 region, (A2, B2) represent the CA3 region, and (A3, B3) represent the DG region. (C) represents histogram of the number of nissel body staining neurons of the contralateral hippocampus injected. Compared with saline group *p<0.05,  p<0.01, * p<0.001 (one-way ANOVA).

Figure 6:
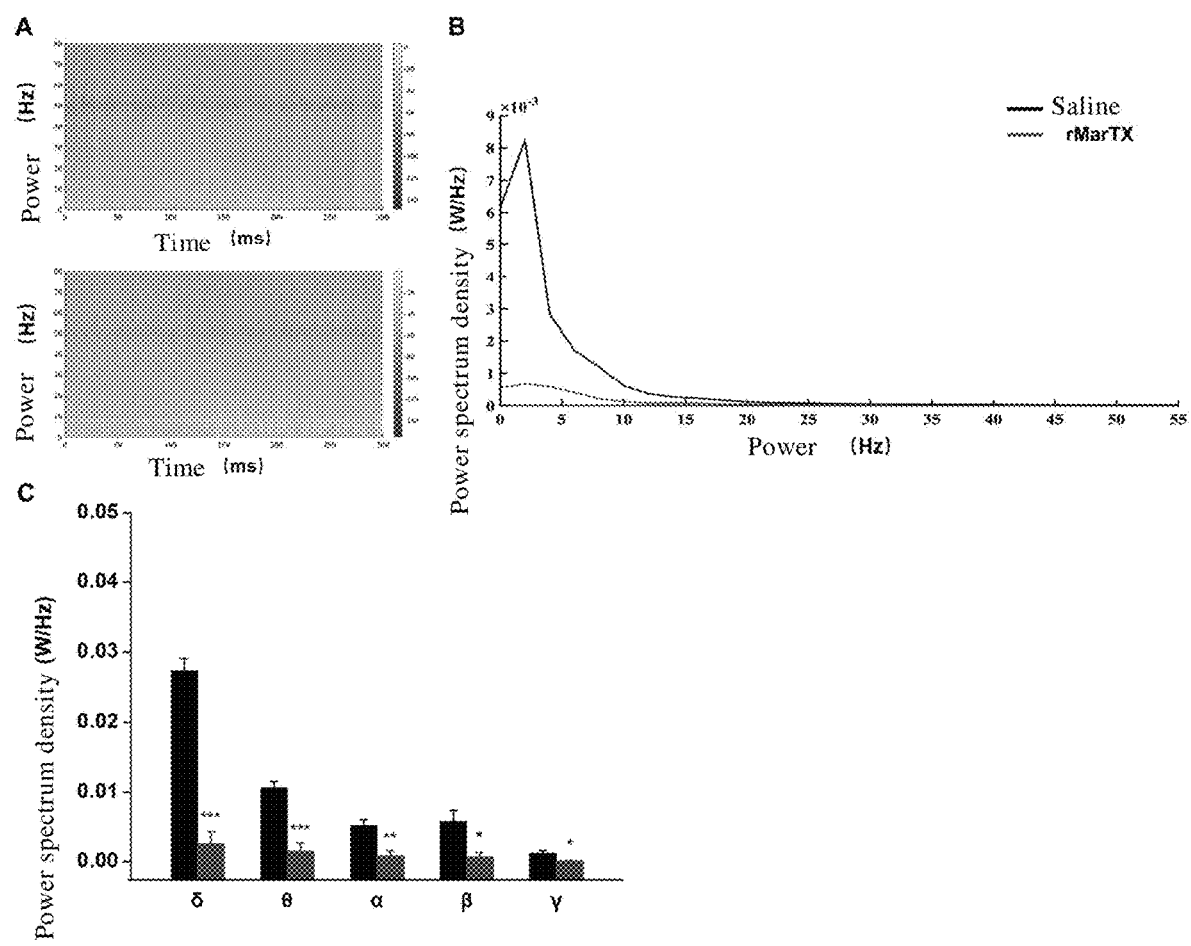

FIG. 6 shows the inhibitory effect of MarTX toxin on PTZ-induced field potential power spectrum density in rat hippocampus.

(A) shows the field potential signal and spectrum heat map of the PTZ epilepsy model in the normal saline group (black) and the MartX toxin group (red), respectively. (B) shows the relationship curves between power spectrum density and brainwave frequency of PTZ epilepsy models in normal saline group (black) and MarTX toxin group (red), respectively. (C) shows the power spectrum density values of brainwaves at different frequencies of $\delta$, $\theta$, $\alpha$, $\beta$ and $\gamma$ waves of PTZ epilepsy models in normal saline group (black) and MarTX toxin group (red), respectively. Compared with saline group *p<0.05, p<0.01,* p<0.001 (one-way ANOVA).

Figure 7:
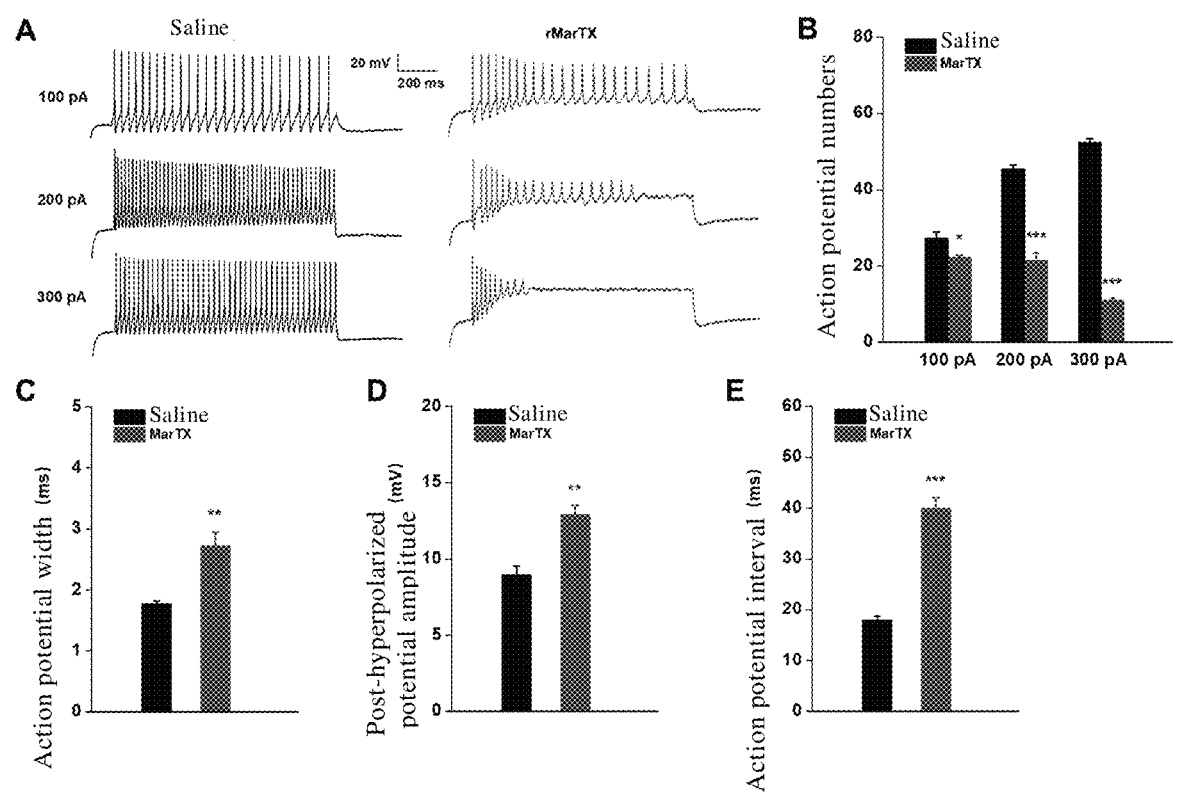

FIG. 7 shows the inhibitory effect of MarTX toxin on PTZ-induced action potential frequency of rat hippocampal neurons.

(A) shows the effect of saline (black) and MarTX toxin (red) on the action potential of hippocampal neurons pre-treated with PTZ. (B) shows the number of action potentials triggered at each current injection. (C) shows the action potential width calculated at half the height of the action potential at 300 pA current injection. (D) shows the post-hyperpolarized potential amplitude calculated from the pre-peak action potential to the post-hyperpolarized peak at 300 pA current injection. (E) shows the action potential interval before the 9th action potential during 300 pA current injection. Compared with saline group *p<0.05, p<0.01, *p<0.001 (one-way ANOVA).

DETAILED DESCRIPTION OF THE INVENTION

After extensive and in-depth research, the inventors accidentally discovered for the first time that a polypeptide substance (i.e. MarTX toxin) can be used to treat and/or prevent epilepsy extremely effectively by screening a large number of different compounds (including a large number of screenings for compounds for sodium ion channels). Experiment results showed that in the rat PTZ (pentetrazol) convulsion model, the inventors found for the first time that MarTX toxin can effectively relieve epilepsy symptoms by measuring the influence of MarTX toxin on recurrent convulsion behavior, the influence on hippocampal c-Fos expression after convulsion seizure in rat, and the investigation of hippocampal neuron damage. On this basis, the present invention was completed.

Martentoxin Protein and Coding Sequence Thereof

As used herein, "Martentoxin protein", "Martentoxin polypeptide", "MarTX toxin" and "MarTX polypeptide", "recombinant MarTX toxin" and "marten toxin" are used interchangeably, referring to a Martentoxin protein. Wild-type Martentoxin protein consists of 37 amino acids having three pairs of disulfide bonds, which is a short-chain polypeptide toxin. In the present invention, the term includes not only wild type but also mutant type; includes not only naturally isolated Martentoxin proteins, but also recombinant Martentoxin proteins, such as recombinantly expressed Martentoxin proteins with or without starting Met, and recombinantly expressed Martentoxin proteins with or without expression tags or enzyme cleavage residues of 1-3 amino acids.

For isolation, Martentoxin can be obtained from *Buthus martensi* Karsch (BmK) venom by isolation and purification.

For recombination, it can be obtained by expression in host cells such as *Escherichia coli* by conventional recombination technology and further isolation and purification.

The amino acid sequence of the wild-type Martentoxin protein is shown in SEQ ID No.: 2:

(SEQ ID No.: 2)
FGLIDVKCFASSECWTACKKVTGSGQGKCQNNQCRCY

A coding sequence of Martentoxin protein is shown in SEQ ID No.: 1

(SEQ ID No.: 1)
tttggactca tagacgtaaa atgttttgca tctagtgaat gttggacagc ttgcaaaaaa 60
gtaacaggat cgggacaagg aaagtgccag aataatcaat gtcgatgcta ctga 114

The amino acid sequence of a recombinant Martentoxin protein is shown in SEQ ID No.: 3:

(SEQ ID No.: 3)
GSFGLIDVKCFASSECWTACKKVTGSGQGKCQNNQCRCY

The experiments of the present invention prove for the first time that MarTX toxin can extremely significantly prevent and treat abnormal excitation of neurons and epilepsy symptoms in a rat PTZ convulsion model, so it is used as a novel polypeptide drug for treating epilepsy symptoms.

It should be understood that although the MarTX polypeptide provided in the examples of the present invention is derived from Buthus martensi Karsch, but MarTX polypeptides from other similar species (especially those belonging to the same family or genus as the Buthus martensi Karsch), whose sequences have a certain homology (conservative) with the sequence in the present invention (preferably, such as SEQ ID NO: 2) can also be used in the present invention.

It should be understood that although the gene provided in the examples of the present invention is derived from Buthus martensi Karsch, but MarTX gene sequences from other similar species (especially those belonging to the same family or genus as the Buthus martensi Karsch), which have a certain homology (conservative) with the sequence in the present invention (preferably, such as SEQ ID NO: 1) are also included in the scope of the invention, as long as the skilled person in the art who has read this application can easily isolate the sequences from other species (especially scorpions) based on the information provided in this application.

The polynucleotides of the present invention may be in the form of DNA or RNA. DNA form includes DNA, genomic DNA, or synthetic DNA, which may be single-stranded or double-stranded. DNA may be a coding strand or a non-coding strand. The coding sequence for mature polypeptides may be the same as that shown in SEQ ID NO: 1 or may be a degenerate variant.

Polynucleotides encoding mature polypeptides include: coding sequences encoding for mature polypeptides only; coding sequences of mature polypeptides and various additional coding sequences; coding sequences (and optional additional coding sequences) and non-coding sequences of mature polypeptides.

The term "polynucleotide encoding polypeptide" may include polynucleotide encoding the polypeptide or polynucleotide further including additional coding and/or non-coding sequences. The present invention also relates to variants of the above polynucleotide, which encode fragments, analogues and derivatives of polyglucoside or polypeptide having the same amino acid sequence as the present invention. The variant of this polynucleotide may be a naturally occurring allelic variant or an unnaturally occurring variant. These nucleotide variants include substitution variants, deletion variants and insertion variants. As known in the art, an allelic variant is an alternative form of a polynucleotide, which may be a substitution, deletion or insertion of one or more nucleotides, but does not substantially change its function of encoding polypeptide.

The invention also relates to polynucleotides that hybridize to the above-mentioned sequences and the two sequences have at least 50%, preferably at least 70%, and more preferably at least 80% identity. The present invention relates in particular to polynucleotides that hybridize to the polynucleotides of the present invention under stringent condition. As used herein, "stringent condition" refers to: (1) hybridization and elution at lower ionic strength and higher temperature, such as 0.2×SSC, 0.1% SDS, 60° C.; or (2) denaturant, such as 50% (v/v) formamide, 0.1% fetal bovine serum/0.1% Ficoll, 42° C., etc., are added during hybridization; or (3) hybridization occurs only when the identity between the two sequences is at least more than 90%, preferably more than 95%.

It should be understood that although MarTX genes of the present invention are preferably derived from Buthus martensi Karsch, but other genes from other species (especially scorpions) that are highly homologous with the MarTX genes of Buthus martensi Karsch (e.g. having more than 80%, such as 85%, 90%, 95% or even 98% sequence identity) are also within the scope of contemplation of the present invention. Methods and tools for aligning sequence identity are also well known in the art, such as BLAST.

Generally, full-length sequence or fragment of MarTX nucleotide of the present invention can be obtained by PCR amplification, recombination or artificial synthesis. For PCR amplification, primers can be designed according to the relevant nucleotide sequences disclosed in the present invention, especially the open reading frame sequences, and a commercially available DNA library or a cDNA library prepared according to conventional methods known to those skilled in the art can then be used as a template to amplify the relevant sequences. When the sequence is long, it is often necessary to perform two or more PCR amplifications, and then splice the amplified fragments together in the correct order. Once the relevant sequence is obtained, the relevant sequence can be obtained in large quantities by recombination method. Generally, it is cloned into a vector, then transferred into cells, and then the relevant sequences are isolated from the proliferated host cells by conventional methods.

In addition, the relevant sequences can also be synthesized by artificial synthesis, especially when the fragment length is short. Generally, fragments with long sequences can be obtained by synthesizing several small fragments first and then connecting them. At present, it has been possible to obtain the DNA sequence encoding the protein (or its fragment, or its derivative) of the present invention entirely by chemical synthesis. Then, the DNA sequence can be introduced into various existing DNA molecules (or e.g. vectors) and cells known in the art. In addition, mutations can also be introduced into the protein sequence of the present invention by chemical synthesis.

The present invention relates to a MarTX polypeptide and variants thereof for the treatment of epilepsy, in a preferred embodiment of the present invention, the polypeptide has an amino acid sequence shown in SEQ ID NO: 2. The polypeptide of the invention can effectively treat and/or prevent epilepsy.

The invention also comprises polypeptides or proteins with the same or similar function that are 50% or more homology (preferably more than 60%, 70%, 80%, more preferably more than 90%, more preferably more than 95%, most preferably more than 98%, such as 99%) with the sequence shown in SEQ ID NO: 2 of the invention.

The "same or similar function" mainly refers to "relieving the symptoms of epilepsy".

The polypeptide of the present invention can be a recombinant polypeptide, a natural polypeptide or a synthetic polypeptide. The polypeptides of the present invention may be naturally purified products, or chemically synthesized products, or produced from prokaryotic or eukaryotic hosts (such as bacteria, yeasts, plants, insects and mammalian cells) by recombinant techniques. According to the host used in the recombinant production scheme, the polypeptide of the present invention may be glycosylated or non-glycosylated. The polypeptide of the present invention may also include or not include an initial methionine residue.

The invention also includes MarTX polypeptide fragments and analogues having MarTX polypeptide activity. As used herein, the terms "fragment" and "analog" refer to polypeptides that retain substantially the same biological function or activity as the native MarTX polypeptide of the present invention.

The polypeptide fragment, derivative or analogue of the present invention may be: (i) a polypeptide having one or more conserved or non-conserved amino acid residues (preferably conserved amino acid residues) to be substituted, and such substituted amino acid residues may or may not be encoded by the genetic code; or (ii) a polypeptide having substituent in one or more amino acid residues; or (iii) a polypeptide formed by fusing mature polypeptide with another compound (such as a compound that prolongs the half-life of the polypeptide, such as polyethylene glycol); or (iv) a polypeptide formed by fusing an additional amino acid sequence to the polypeptide sequence (such as a leader sequence or secretion sequence or a sequence or pro-protein sequence used to purify the polypeptide, or a fusion protein). These fragments, derivatives and analogues fall within the scope known to those skilled in the art according to the definition herein.

In the present invention, the polypeptide variant is an amino acid sequence as shown in SEQ ID NO.: 2, a derivative sequence obtained by substituting, deleting or adding several (usually 1-10, preferably 1-8, more preferably 1-4, preferably 1-2) or at least one amino acid, and a sequence adding one or more (usually less than 10, preferably less than 5, more preferably less than 3) amino acids to the C-terminal and/or N-terminal. For example, substitution with amino acids of similar properties in the protein generally does not change the function of the protein, and the addition of one or more (e.g., 1-3) amino acids to the C-terminal and/or N-terminal generally does not change the function of the protein. These conservative variations are preferably produced by substitution according to Table 1.

TABLE 1

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The invention also includes analogues of the claimed protein. These analogs differ from natural SEQ ID NO: 2 either in amino acid sequences or in modification forms that do not affect the sequences, or both. Analogues of these proteins include natural or induced genetic variants. Induced variants can be obtained by various techniques, such as random mutagenesis by radiation or exposure to mutagens, site-directed mutagenesis or other known molecular biology techniques. Analogues also include analogues having residues different from natural L-amino acids (e.g., D-amino acids), and analogues having non-naturally occurring or synthetic amino acids (such as β and γ-amino acids). It should be understood that the proteins of the present invention are not limited to the representative proteins listed above.

Modifications (usually without changing the primary structure) include chemically derived forms of proteins in vivo or in vitro, such as acetylation or carboxylation. Modifications also include glycosylation, such as those carried out during protein synthesis and processing. This modification can be accomplished by exposing the protein to enzymes that perform glycosylation, such as mammalian glycosylase or deglycosylase. Modifications also include sequences having phosphorylated amino acid residues (such as phosphotyrosine, phosphoserine, phosphothreonine).

Pharmaceutical Composition and Method of Administration Thereof

The present invention provides a pharmaceutical composition comprising a pharmaceutically acceptable carrier and an effective amount of the following active ingredient: MarTX toxin or the active fragment thereof and pharmaceutical active ingredients for treating and/or preventing epilepsy.

As used herein, the term "effective amount" or "effective dose" refers to an amount acceptable to a human and/or animal that is capable of producing a function or activity for a human and/or an animal.

As used herein, a "pharmaceutically acceptable" ingredient is a substance suitable for use in human and/or mammal without excessive adverse side effects (e.g., toxicity, irritation, and allergy), i.e., having a reasonable benefit/risk ratio. The term "pharmaceutically acceptable carrier" refers to a carrier used for the administration of therapeutic agent, including various excipients and diluents.

The pharmaceutical composition of the present invention contains a safe and effective amount of the active ingredient of the present invention and a pharmaceutically acceptable carrier. The carriers include, but are not limited to, saline, buffer, glucose, water, glycerol, ethanol, and combinations thereof. Generally, the pharmaceutical formulation should be matched with the administration mode, and the dosage form of the pharmaceutical composition of the present invention is an injection. For example, the composition can be prepared by conventional methods with normal saline or aqueous solutions containing glucose and other adjuvants. The pharmaceutical composition should be manufactured under sterile conditions.

The effective amount of the active ingredient according to the present invention can vary according to the mode of administration and the severity of the disease to be treated, etc. The selection of the preferred effective amount may be determined by one of ordinary skill in the art based on various factors (e.g., through clinical trials). The factors include but are not limited to: pharmacokinetic parameters of the active ingredient, such as bioavailability, metabolism, half-life, etc.; the severity of the disease to be treated, the weight of the patient, the immune status of the patient, the route of administration, etc. For example, due to the urgent requirements of treatment conditions, separate doses can be given several times a day, or the doses can be reduced proportionally.

Pharmaceutically acceptable carriers of the present invention include but are not limited to water, saline, liposome, lipids, protein, protein-antibody conjugate, peptides, cellulose, nanogel, and combinations thereof. The selection of the carrier should be matched to the mode of administration, which is well known to the ordinary skill in the art.

The first active ingredient (a) MarTX toxin or the active fragment thereof provided by the present invention can be combined with the second active ingredient (b) other drugs for treating and/or preventing epilepsy. Wherein the second active ingredient (b) is an antiepileptic drug already available in the prior art, which includes but is not limited to carbamazepine, fluoropyridine, gabapentin, lamotrigine, oxcarbazepine, phenytoin, phenytoin sodium, retigabine, topiramate, sodium 2-propylpentanoate, ethosuximide, sodium valproate, and combinations thereof.

C-Fos Gene

C-Fos Gene is one of immediate early genes [Trends Neurosci. 1995, 18, 66-67] (IEGs, a proto-oncogene that can be induced by the second messenger), which is closely related to various pathophysiological processes after the onset of epilepsy. Under physiological conditions, c-Fos Gene is expressed at a low level in the central nervous system; when neurons are stimulated physically or chemically, neurons are excited and they activate IEGs such as C-Fos etc., mRNA generated by IEGs transcription translates into c-Fos protein [Annu. Rev. Neurosci. 1991, 14, 421-451], etc. This protein can regulate the expression of a variety of late-response genes (LRGs), and at the same time can lead to epileptic seizures through a variety of mechanisms, eventually leading to the formation of epileptic lesions [Neuron 1990, 4, 477-485]. C-Fos protein is rapidly expressed in large quantities during epileptic seizures. If drugs or other therapeutic methods are used to control epileptic seizures, the expression of this protein can be significantly inhibited. Therefore, the determination of c-Fos expression can be used as an effective indicator for the mechanism of action and the evaluation of curative effect of antiepileptic drugs.

Nissel Body

Nissel body is a special easily stained substance found in the cytoplasm of neuron dendrites. In general, the Nissel body has a fixed shape, wherein the neuron cell body is large, the cytoplasm is pale and uniformly stained, the nucleus is large and round, and all cells are stained dark. The pyramidal cells are closely arranged in the dentate gyrus (DG) of hippocampus, with 4 or 5 layers of cells. However, when the brain is damaged, their morphology will change, and the blurring of cell edges will reduce the integrity of cells. At the same time, the staining of cell bodies will become lighter, the distribution of neurons will become disordered, and the number of cells or cell layers will become less. Therefore, the existence, distribution and pathological changes of neurons can be identified by the shape and number of Nissel bodies.

PTZ (Pentylenetetrazole)

Pentylenetetrazole (PTZ), also known as pentetrazol, pentetrazole and cardiazole, is a white crystalline powder chemical. The chemical name is 1, 5-pentamethylene-1H-tetrazole, molecular formula is $C_6H_{10}N_4$, molecular weight is 138.1704. Pentylenetetrazole is a central excitant, which is mainly used clinically to rescue central respiratory failure caused by severe barbiturate and narcotic intoxications; it can also be used for respiratory depression and acute circulatory failure caused by acute infectious diseases, anesthetics and barbiturates intoxications.

Pentylenetetrazole can excite the respiratory center and cardiovascular movement center, and its effect is rapid and intense, making the respiration deepen and accelerate, and the blood pressure rises slightly. If the dose is slightly larger, the excitement can extend to cerebral cortex and spinal cord, causing convulsion.

PTZ mainly acts on chloride ion channel of $GABA_A$ receptor (γ-aminobutyric acid A-type receptor) to inhibit the activity of GABA neurons, thus excessively enhancing the excitability of nervous system and inducing clonic or generalized tonic epilepsy in animals and humans. PTZ-induced rodent seizure model has been widely used in the study of epilepsy mechanism and new antiepileptic drugs.

In the present invention, convulsion/epilepsy is induced by intraperitoneal injection of PTZ into animals, so as to conduct a subsequent experimental study on the effect of MarTX toxin of the present invention on epilepsy.

The Main Advantages of the Present Invention Include:

(1) MarTX toxin has the characteristics of strong effect and small dosage (the dosage can be as low as 0.32 μg/kg in rat PTZ model), which not only significantly prolongs the incubation period of seizures, but also significantly relieves the symptoms of epilepsy (especially can significantly reduce the incidence of Grades 3, 4 and 5 epilepsy), so it can be used as a new polypeptide drug for epilepsy treatment.

(2) The recombinant MARTX toxin can be expressed and prepared by prokaryotic recombination, and is expected to provide a safe, effective and inexpensive antiepileptic drug for epilepsy patients.

(3) MarTX toxin is a neurotoxin with very small molecular weight (only about 4 KDa), which can effectively act on the brain through the blood-brain barrier.

(4) MarTX toxin is a highly specific neurotoxin which is selective for a+B 4 subtype ion channels, large-conductance calcium- and voltage-activated potassium channels, but has no effect on cardiovascular, endocrine and reproductive systems, so the side effects are small.

(5) MarTX toxin is the first polypeptide substance proved by experiments to have the effect of relieving epilepsy.

The present invention will be further illustrated below with reference to the specific examples. It should be understood that these examples are only to illustrate the invention but not to limit the scope of the invention. The experimental methods without specific conditions in the following examples usually follow conventional conditions, such as Sambrook et al., Molecular Cloning: Laboratory Manual (New York: Cold Spring Harbor Laboratory Press, 1989), or according to the conditions recommended by the manufacturer. Unless indicated otherwise, parts and percentage are calculated by weight.

Unless otherwise specified, the materials and reagents used in the Examples are commercially available.

Experimental Materials and Methods

Experimental Animals and Drugs

Experimental animals: adult male SD rats (provided by Shanghai Experimental Animal Center, Chinese Academy of Sciences), 250-300 g, 5 rats in each cage, raised under routine laboratory conditions, and the room temperature was maintained at 22±1° C., with natural circadian rhythm.

Related Drugs: see Preparation Example 1 for expression and purification of recombinant *Buthus martensi* Karsch toxin Martentoxin (MarTX toxin for short).

Pentylenetetrazole (PTZ, CAS: 54-95-5) was purchased from Sigma Company, USA.

Operation Animal

After anesthesia by intraperitoneal injection of 10% chloral hydrate (300 mg/kg), the rats were fixed on a stereotaxic instrument (NS-2, Narishige, Japan), the hair on the top of the head was shaved and the scalp was disinfected, the skin was cut and the subcutaneous tissue was cauterized with 10% hydrogen peroxide to expose the Bregma point of the skull. According to the rat brain coordinates map, the implantation point of the dosing base (AP-4. 3 mm, L 2.2 mm) was determined on the skull. After the position was determined, a small hole (1 mm) was drilled with a dental drill, the inner plate was stripped off, the cerebral dura mater was picked out by the needle tip, and the dosing base cannula was implanted into the hippocampal CA1 region 2.5 mm below the skull. The base was fixed to the surface of rat skull by dental cement.

Preparation Example 1

A DNA sequence (SEQ ID No.: 4) expressing His-MBP-Thrombin site-MarTX fusion protein was synthesized by an artificial synthesis method. SEQ ID No.: 4 was digested with Nco I and Not I enzymes and ligated with the same enzyme digested pETDuet-1 plasmid to obtain the recombinant pETDuet-1-MarTX plasmid. The recombinant plasmid was transformed into E. coli Origami B (DE3) expression strain for prokaryotic expression.

After recombinant expression, a fusion protein (sequence shown as SEQ ID No.: 5) was obtained, and the MarTX polypeptide was prepared by the following method.

The specific purification method steps were as follows:

1) The fusion protein in Buffer A environment was first bound to the nickel column, and then gradient elution was performed with Buffer B imidazolium salt solution to remove most of the heteroproteins. The first affinity column purification was completed and detected by SDS-PAGE electrophoresis.

2) The collected target fusion protein (about 46.8 kDa) was dialyzed and digested at 18° C. in 2 L Buffer C, then Thrombin enzyme was added at 6 U/mL, and the enzymes were stirred and digested overnight in 3.5 kDa dialysis bags.

3) The digestion mixture was then loaded onto an Amylose Resin chromatography column using a constant flow pump, and the cross-flow component (FL) and the Buffer D elute component were collected. His-MBP-tag was eluted by Buffer E. The second affinity column purification was completed and detected by SDS-PAGE electrophoresis.

4) The FL component and Buffer D elute (usually containing small amounts of recombinant MarTX toxin) were then concentrate to 2 mL for further gel column purification.

5) The gel chromatography column Superdex 75 was pre-balanced with Buffer F, then the sample was loaded onto the column and eluted with Buffer F. The elution peak with a retention volume of about 110 mL was collected to obtain the recombinant MarTX toxin sample, and the previous absorption peak was MBP-tag or uncut fusion protein.

MarTX toxin with high purity was obtained, and the sequence was shown as SEQ ID No.: 3.

The relevant buffer components in the purification process were shown in Table 2.

TABLE 2

Relevant buffers during purification of recombinant MarTX toxin

| Buffer Name | Buffer components |
| --- | --- |
| Buffer A | 25 mM Tris, 500 mM NaCl, pH 7.50 |
| Buffer B | 25 mM Tris, 500 mM NaCl, 500 mM imidazole, pH 7.50 |
| Buffer C | 25 mM Tris, 150 mM NaCl, pH 7.50 |
| Buffer D | 25 mM Tris, 150 mM NaCl and 0.5 mM EDTA, pH 7.50 |
| Buffer E | 25 mM Tris, 150 mM NaCl and 0.5 mM EDTA, 300 mM Maltose, pH 7.50 |
| Buffer F | 25 mM NaH$_2$PO4, 100 mM NaCl, pH 6.80 |

Example 1: Effect of MarTX Toxin on Recurrent Convulsive Behavior of PTZ in Rat 1.1 Experimental Steps Adult male SD rats were placed in a transparent glass box of 40×30×50 cm to observe the convulsive reaction after administration. Before injection, rats were placed in the box 1 h in advance, moved freely to adapt to the environment, and then injected PTZ (60 mg/kg) intraperitoneally to induce convulsion in rats. The experiment was divided into toxin injection group and normal saline blank control group.

(1) MarTX toxin injection group: after one intraperitoneal injection of PTZ to induce seizures of epilepsy, the rats were injected with MarTX toxin (dissolved in 2 μL normal saline) in the hippocampus the next day, and then the PTZ was injected again. The toxin dose was 0.08 μg, n=7-8 (n is the number of experimental rats);

(2) Normal saline blank control group: after one intraperitoneal injection of PTZ to induce seizures of epilepsy, the rats were injected with the same amount of normal saline into the hippocampus one day later, and then PTZ was injected again, n=6.

In the experiment, "double-blind" dosing and animal behavioral study were used to reduce human error. Incubation period, mortality, duration and number of seizures under different severity of seizures were measured as statistical indexes. The severity of seizures in rats was rated according to the following criteria [Neurophysiol. 1972, 32, 281-294; Brain Res. 1997, 758, 92-98]:

Grade 0: no response;

Grade 1: rhythmic twitch of mouth and face;

Grade 2: wave-like migratory spasm of body;

Grade 3: systemic myoclonus and hip upturned;

Level 4: the body turned to one side;

Grade 5: inverted position, systemic rigidity spasticity seizure.

A complete convulsive seizure was defined as the period from the onset of the seizure to the return to normal after the seizure. The interval of more than 5 s between seizures was defined as another independent seizure. Incubation period was defined as the time from PTZ injection to the beginning of the first grade 2 seizure.

1.2 Experimental Results

Compared with normal saline blank control group, the regulatory effect of MarTX toxin on recurrent convulsion behavior of PTZ in rats was investigated, and the experimental results were shown in Table 2.

TABLE 2

Inhibitory effect of MarTX toxin on recurrent convulsive behavior of PTZ within 2 h

|  | Normal saline | MarTX | Relative amplitude |
|---|---|---|---|
| Number of animals (n) | 6 | 6 | |
| Number of deaths | 0/6 | 0/6 | |
| Incubation (s) | 157.33 ± 33.63 | 427.17 ± 62.21** | 272% |
| Duration of epilepsy (s) | 400.00 ± 97.57 | 160.00 ± 38.47* | 40% |
| Frequency of epileptic seizures | | | |
| The number of seizures from Grade 1 to Grade 2 | 10.33 ± 4.59 | 4.33 ± 1.36 | 42% |
| The number of Grade 3 seizures | 3.67 ± 0.95 | 0.50 ± 0.22** | 14% |
| The number of seizures from Grade 4 to Grade 5 | 2.17 ± 0.40 | 0.50 ± 0.34* | 23% |

One-way ANOVA results showed that there were significant differences (*$P < 0.05$, **$P < 0.01$) in the incubation period, duration and frequency of seizures in the MarTX toxin group compared with the normal saline control group.
Table 2 shows that :(1) compared with the blank control group, the incubation period of recurrent convulsion in the MarTX toxin group was significantly prolonged (the incubation period of the MarTX toxin group was 427.17 ± 62.21 s, n = 6, **$P < 0.01$; 157.33 ± 33.63 s in normal saline group, n = 6).
(2) MarTX toxin also significantly reduced the duration of epilepsy (duration of MarTX group: 160.00 ± 38.47 s, n = 6, *$P < 0.05$; control group was 400.00 ± 97.57 s, n = 6) by about 60%.
(3) In terms of frequency of epileptic seizures, MarTX toxin could significantly reduce various grades of seizures, especially Grade 3, Grade 4 and Grade 5 seizures. 0.08 μg of MARTX toxin significantly reduced the number of epileptic seizures (Grade 4 &5) (MarTX group was 0.50 ± 0.34 times, n = 6, * $P < 0.05$; the control group was 2.17 ± 0.40 times, n = 6), with a decrease of 77% (100% − 23% = 77%). As for the number of Grade 3 seizures, the number of epileptic seizures in the MarTX group was also significantly reduced (** $P < 0.01$) by 86%, compared with the blank control group.

Therefore, the MarTX toxin of the present invention showed significant inhibitory effect on the incubation period and duration of seizures and the number of seizures under different severity of seizures, indicating that MarTX toxin can effectively relieve the abnormal excitability of neurons and epileptic symptoms.

Example 2 Effect of MarTX Toxin on c-Fos Expression in Hippocampus after Seizures in Rats 2.1 Experimental Steps After the completion of the PTZ-induced epileptic status behavior experiment, the animals were anesthetized by intraperitoneal injection of sodium pentobarbital (60 mg/kg). The blood vessels were washed by perfusion of 200 mL normal saline through the ascending aorta of the left ventricle, and then perfused with 400 mL fixative solution (0.1M PBS containing 40% paraformaldehyde, pH7.4, 4° C.) for 1-2 h. After the brain tissue was removed and placed in the same fixative overnight, it was immersed in 20% sucrose solution until it sank to the bottom of the container, and then immersed in 30% sucrose solution until it sank to the bottom of the container.

The hippocampal region was secreted from the brain of the rats using a refrigerator slicer (Leica 1900, Germany) with a thickness of 20 μm. The slices were pasted on gelatin-chromium potassium sulfate treated glass slide and frozen at −20° C. for later use. C-Fos immunohistochemistry was performed as follows:
  (1) The slice was taken out of the −20° C. refrigerator, reheated for 30 min, framed with a histochemical pen around the slice, and dried;
  (2) The slices were immersed for 30 min for braking membrane in 1% Triton-X solution added with 1% $H_2O_2$;
  (3) Rinsed 3 times with 0.01M PBS (pH7.4) buffer, 5 min for each time;
  (4) Sealed with 5% Goat serum at 37° C. for 1 h;
  (5) The serum was sucked dry with filter paper, rabbit anti-c-Fos antibody (1: 400, Sc-52, Santa Cruz, USA) was added, the antibody was diluted with 0.01 M PBS, 100 μL for each section, and incubated in a wet box at 4° C. for 48 h;
  (6) Rinsed with 0.01 M PBS (pH 7.4) for 10 min and repeated 3 times;
  (7) Biotin-labeled goat anti-rabbit IgG diluted with 0.01 M PBS (1:200) was added at room temperature for 2 h;
  (8) Rinsed with 0.01 M PBS for 10 min and repeated 3 times. ABC complex (A:B:PBS=1:1:100) was added at room temperature for 2 h;
  (9) Rinsed with 0.01 M PBS (pH 7.4) for 10 min and repeated 3 times;
  (10) Stained in the dark by DAB-nickel sulfate amine-glucose oxidase (DAB, Sangon Biotech) for 10 min;
  (11) Dehydration, 70%, 80%, 95%, 100% (×2) were used for dehydration, 5 min each time, and then soaked with xylene twice, 5 min each time;
  (12) The expression of c-Fos was observed under a microscope and sealed with neutral gum.

The number of c-Fos-like immunoreactive (FLI) neurons in different hippocampal regions (CA1, CA3) and dentate gyrus (DG) was counted. Two groups of animals (6 animals in each group) were randomly selected from 6 to 8 sections for FLI counting in different regions (counting respectively on the same side and the other side of injected toxin or normal saline), and the average value was calculated at last. The inhibition rate of c-Fos expression was calculated according to the following formula.

$$\text{Inhibitory ratio} = (A-B)/A \times 100\%$$

Wherein, A represents the number of FLI neurons in the normal saline control group; B represents the number of FLI neurons in the MarTX toxin injection group in the corresponding region of the hippocampus.

2.2 Experimental Results

Figure 1:
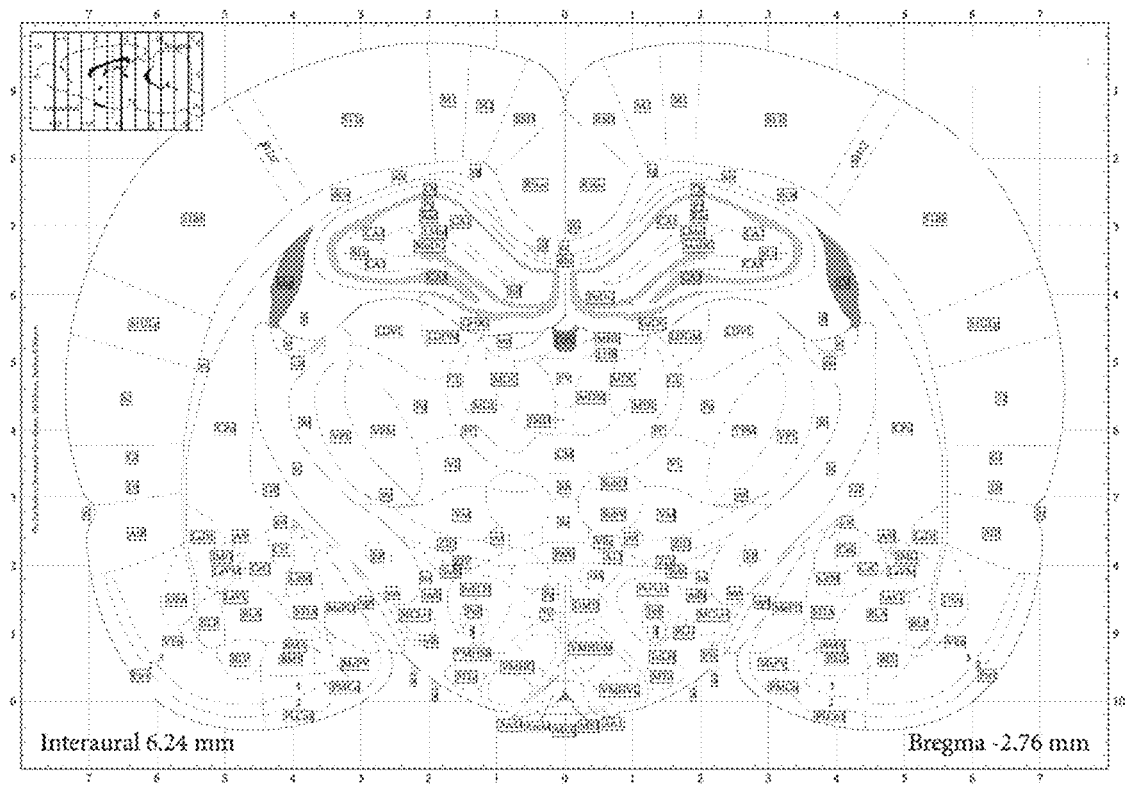
FIG. 1 shows the rat brain atlas [*The rat brain in stereotaxic coordinates.* 2007].

Rat hippocampus can be divided into hippocampal gyrus and dentate gyrus (DG) according to different cell morphology. The hippocampal gyrus mainly consists of CA1 (*cornu ammonis*), CA2, CA3 and hilar regions, which are mainly composed of some pyramidal neurons. The CA1 region is connected with the subiculum, and the hilar region is adjacent to the dentate gyrus. Dentate gyrus is the dentate cortex between hippocampal fissure and hippocampal fimbria, which is C-shaped. Its structure is divided into three layers: molecular layer, granular cell layer and polymorphic layer, which are basically composed of granular cells. Refer to FIG. 1 for specific location [*The rat brain in stereotaxic coordinates.* 2007].

Figure 2:
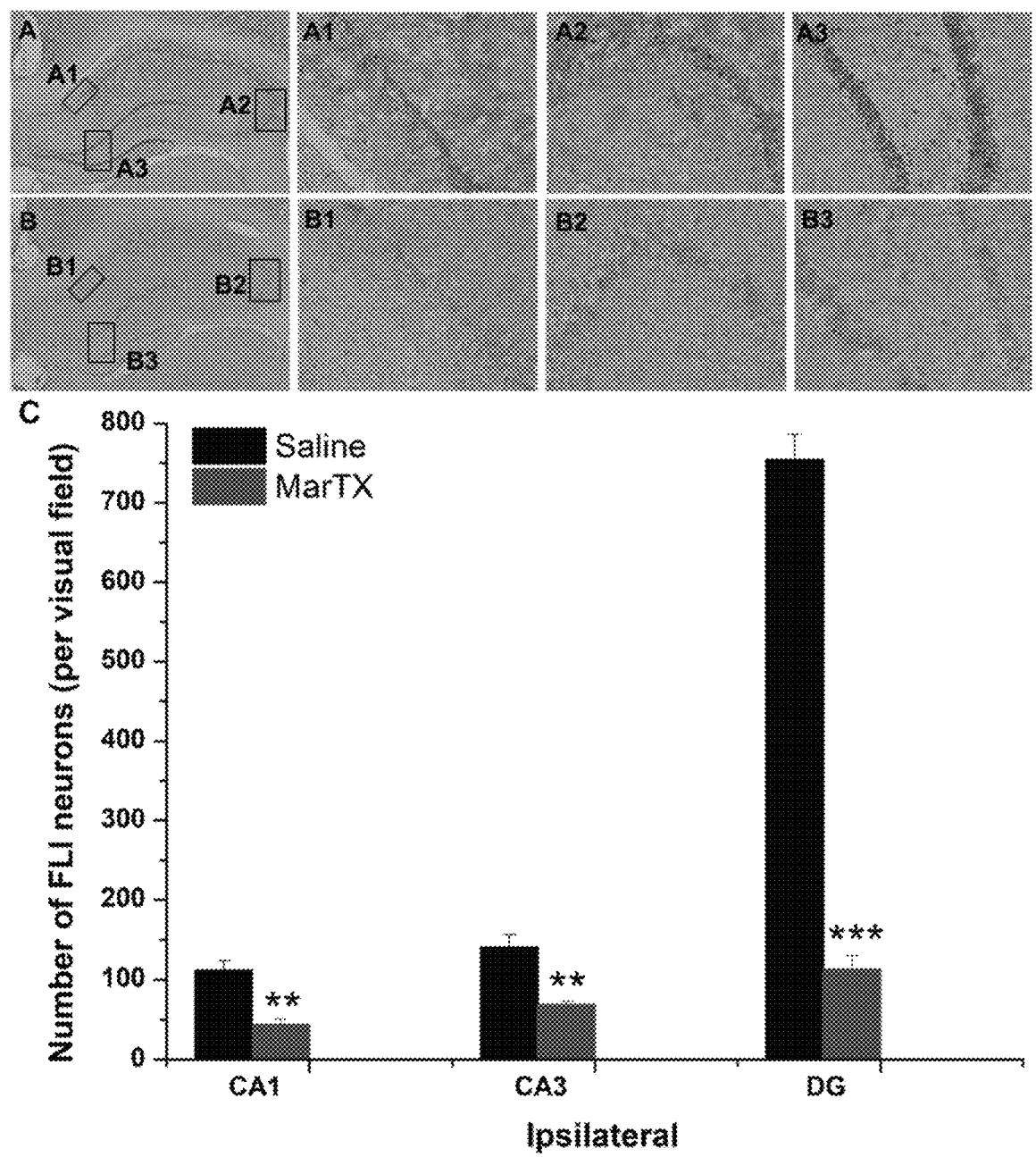
FIG. 2 shows the inhibitory effect of MarTX toxin on c-Fos expression induced by PTZ injection in ipsilateral hippocampus.

The expression of c-Fos in hippocampus of rats after epilepsy was measured according to the above experimental steps and data processing methods. The experimental results were shown in FIGS. 2 and 3.

The analysis results were as follows: (1) after the PTZ-induced epileptic status behavior experiment, all animals including normal saline control group and toxin injection group showed c-Fos protein expression in ipsilateral and contralateral hippocampus of injection site, see FIGS. 2 and 3;

(2) In the normal saline control group, c-Fos positive neurons were mainly concentrated in the granulosa cell layer of hippocampal DG region, and there were few positive neurons in CA1 and CA3 regions;

(3) Martx toxin can significantly inhibit the expression of PTZ-induced c-Fos in hippocampus. Compared with the normal saline control group, the inhibitory rates of MarTX on CA1, CA3 and DG regions injected into the ipsilateral hippocampus were 60.71%, 51.18% and 84.98%, respectively, see FIG. 2. The inhibitory effect of MarTX on the expression of c-Fos in the ipsilateral hippocampus was stronger than that in the contralateral hippocampus (compared with the normal saline control group, the inhibitory rates of MarTX on the CA1, CA3 and DG regions of the contralateral hippocampus were 54.01%, 55.25%, and 78.53%, respectively), see FIG. 3.

Therefore, the MarTX toxin had a significant inhibitory effect on the expression of c-Fos protein in the hippocampus of rats after PTZ-induced epilepsy, and the injection effect on the ipsilateral hippocampus was stronger than that on the contralateral hippocampus, indicating that the MarTX toxin of the present invention may have anti-epilepsy drug effect.

Example 3: Investigation of Hippocampal Neuron Damage after Seizures in Rats 3.1 Experimental Steps (1) The slice was taken out of the −20° C. refrigerator, reheated for 20 min, framed with a histochemical pen around the slice, and dried;

(2) The slice was soaked in distilled water for 2 min;

(3) Nissel staining solution (purchased from Beyotime) was dropped on the brain slice, and dyed in a 37° C. water bath for 10 min;

(4) Washed twice with distilled water for 10 s each time;

(5) Sections were dehydrated with 70%, 80%, 95%, 100% alcohol, 2 min each time, and then soaked with xylene twice, 5 min each time;

(6) The nissel body staining was observed under a microscope and sealed with neutral gum.

The above two groups of animals (6 animals in each group) were randomly selected from 6 to 8 sections to count the neuron cells in different hippocampal regions (CA1, CA3 and DG). Finally, the average value was taken and the increasing rate of the number of neurons was calculated.

3.2 Experimental Results

The damage or death of hippocampal neurons after PTZ-induced epilepsy in rats was measured by Nissel staining test. The experimental results were shown in FIGS. 4 and 5.

The analysis results were as follows: (1) The MarTX toxin group retained a relatively complete hippocampal structure, and the neurons in hippocampal region, especially in DG region, had the highest density and organized closely, with the deepest nissel body staining. In contrast, the arrangement of neurons in the normal saline group become loose, the cell density was reduced, and the staining was the lightest, indicating that the damage to neurons in the normal saline control group after PTZ-induced epilepsy was the greatest, while the MarTX toxin of the present invention protected hippocampal neurons after epilepsy, and the damage was the smallest;

(2) The neuronal increase rates of CA1, CA3 and DG regions in the ipsateral hippocampus of the MarTX toxin group and the normal saline group were 95.73%, 102.02% and 93.43%, respectively, as shown in FIG. 4, and the ineuronal increase rates of CA1, CA3 and DG regions of the contralateral hippocampus were 79.50%, 94.82% and 79.62% respectively, as shown in FIG. 5, indicating that the protective effect of MarTX on the neurons of the ipsateral hippocampus injection was stronger than that of the contralateral hippocampus.

In conclusion, PTZ-induced epileptic status could cause damage or death of hippocampal neurons in rats. After measurement, it was found that the damage degree of neurons in the experimental group injected with MarTX was greatly reduced, and the number of neurons stained by Nissel was the largest and the arrangement was the closest.

The above experiments jointly showed that the MarTX toxin of the present invention can inhibit the seizures of rats in behavior, inhibit the expression of c-Fos in the hippocampus at the same time, and reduce the damage degree of hippocampal neurons, indicating that the MarTX toxin of the present invention had anti-epileptic effect.

Example 4 Investigation of Field Potential in Hippocampus after Seizure in Rats 4.1 Experimental Steps Microarray electrodes were implanted according to the sixth edition of "Rat Brain Stereotactic Atlas" (FIG. 1) edited by George Paxinos and Charles Watson to determine the position of the electrodes: AP: 4.3 mm, MR: 2.2 mm, DV: 2.5 mm, and 3-4 screws were fixed in the blank region of the skull as reference electrodes. The recording electrode and electrode base were fixed with dental cement. Field potentials (FP) were recorded after waking rats. FP signal and sync video could be recorded via omniplex (plexon, USA). According to Nesquet's sampling theory, the back end of the electrode was connected to a preamplifier and coupled to the analog-to-digital converter box. 1 Hz was taken as the sampling frequency of local field potential recording, and a 50 Hz high-pass filter and a 300 Hz low-pass filter were set for continuous recording for more than 30 minutes. The local field potential recording results were exported to *.pl2 file format, and visual preview was carried out using offline sorter v4 software. The same channel was used to analyze the local field potential, and the data were derived by MATLAB (MathWorks, USA) program. The local field potential signals of different frequencies were decomposed by wavelet transform to obtain the circadian rhythms of different frequencies ($\delta$: ~0-4 Hz, $\theta$: ~4-8 Hz, $\alpha$: ~8-13 Hz, $\beta$: ~13-30 Hz, $\gamma$: ~30-100 Hz). In the power spectrum analysis, Welch, Hamming window and Fast Fourier Transform methods were used to calculate the change of power spectral density of local FP.

4.2 Experimental Results

The regulatory effect of normal saline and MarTX on field potential signals in PTZ epilepsy model was compared. The spectrum density heat map generated by omniplex software (plexon, USA) was used to observe the change of power spectrum density of FP. Compared with normal saline group, MarTX could rapidly inhibit FP power spectrum density in PTZ-induced epileptic rats (FIGS. 6A and B). In the power spectrum density graph (FIG. 6B), a peak appeared in the low frequency ($\delta$) band in the normal saline group, while this peak could not be observed in the MarTX group, indicating that the application of MarTX suppressed the neural network that produced the low frequency waves. According to statistics, the power spectrum density of brain $\delta$ wave ($P<0.001$, $n=3$), $\theta$ wave ($P<0.001$, $n=3$), $\alpha$ wave ($P<0.01$, $n=3$), $\beta$ wave ($P<0.05$, $n=3$) and $\gamma$ wave ($P<0.05$, $n=3$) in the MARTX group were significantly lower than those in the normal saline group (FIG. 6C).

Example 5 Patch Clamp Current Record and Action Potential Analysis of Rat Hippocampal Neurons 5.1 Experimental Steps If the resting membrane potential of the cell was −70 mV and the input resistance was 350MΩ or more, the patch clamp current was considered acceptable. The record was held at −80 mV as the holding current and induced by increasing positive current injection (for 1000 ms). The action potential differences between PTZ treated cells (measured 24 h after application) and PTZ treated epileptic cells (measured 10 min after application) treated with rMarTX were compared. The peak width was measured at half the peak amplitude of the action potential. The difference between the peak threshold value and the minimum voltage after the peak value of the action potential was used as the measurement value of the post-superpotential. Peak interval was the time between action potential peaks.

In the current patch clamp recording, the standard external solution was composed of 1.2 mM $MgCl_2$, 10 mM HEPES, 10 mM glucose, 1.5 mM $CaCl_2$, 2.5 mM KCl and 145 mM NaCl. The pH of the solution was adjusted to 7.4 with NaOH. The internal solution was composed of 1 mM $CaCl_2$, 4 mM $MgCl_2$, 10 mM HEPES, 11 mM EGTA, and 140 mM KCl. The pH of the solution was adjusted to 7.2 with KOH.

5.2 Experimental Results

Pentylenetetrazole (PTZ) could induce BK channel function acquisition and high discharge rate of pyramidal neurons in neocortex and hippocampus. Therefore, we compared the change of action potential characteristics caused by current injection in PTZ-induced pre-epileptic cells after application of normal saline and MarTX (FIG. 7A-E). FIG. 7A showed the examples action potential curves of neurons pretreated with PTZ after application of saline and MarTX, respectively. Current injection into hippocampal pyramidal neurons could induce the generation of action potential, and its trigger frequency may be limited by two mechanisms. One is that the peak interval during current injection increases with time, resulting in the decrease of action potential. The other is a higher current injection, such as 300 Pa, resulting in the failure of the action potential. We found that the interval between peak action potentials of epileptic cells pretreated with PTZ (normal saline group) was shorter (FIG. 7E). The action potential peak interval of epileptic cells treated with MarTX (MarTX group) was significantly longer than that of PTZ pretreated cells (FIG. 7A) (FIG. 7E, $P<0.001$, n=4). In addition, epileptic cells treated with MarTX resulted in more action potential failure at higher current injection (300 pA) (FIG. 7A), which was completely different from PTZ pretreated epileptic cells (normal saline group) (FIG. 7A). Thus, compared with PTZ pretreated epileptic cells (normal saline group), the longer the action potential peak interval, the greater the action potential width of the epileptic cells treated with MarTX (FIG. 7C, $P<0.01$, n=4). The occurrence of action potential failure leads to a significant decrease in the discharge rate of the epileptic neurons treated with MarTX (FIG. 7B, $P<0.001$ at 200 and 300 pA, $P<0.05$ at 100 pA trace, n=4). We also found that the MarTX treatment significantly increased the amplitude of the post-hypertrophy potential (FIG. 7D, $P<0.01$ at the 300 pA curve, n=4).

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A method of treating epilepsy in a subject in need thereof, comprising administering to the subject a composition comprising a MarTX toxin or a pharmaceutically acceptable salt thereof, wherein the MarTX toxin consists of the amino acid sequence of SEQ ID NO: 3.

2. The method of claim 1, wherein the epilepsy is caused by abnormal excitation of neurons.

3. The method of claim 1, wherein the composition is a pharmaceutical composition.

4. The method of claim 3, wherein the pharmaceutical composition is in a dosage form for injection.

5. The method of claim 3, wherein the pharmaceutical composition is administered intravenously, subcutaneously, intramuscularly, or intracranially.

6. The method of claim 4, wherein the pharmaceutical composition is administered by microinfusion pumps.

7. The method of claim 4, wherein the pharmaceutical composition is administered by intracranial administration.

8. The method of claim 7, wherein the pharmaceutical composition is administered to the ipsilateral hippocampus of the subject.

9. The method of claim 3, wherein the pharmaceutical composition is administered intravenously or intracranially.

10. The method of claim 1, wherein the MarTX toxin is a recombinant polypeptide produced from *Escherichia coli.*

11. The method of claim 1, wherein the composition is administered in combination with another agent.

12. The method of claim 11, wherein the composition is administered in combination with another agent for the treatment of epilepsy.

13. The method of claim 12, wherein the another agent is selected from the group consisting of: carbamazepine, fluoropyridine, gabapentin, lamotrigine, oxcarbazepine, phenytoin, phenytoin sodium, retigabine, topiramate, ethosuximide, sodium valproate, and combinations thereof.

14. The method of claim 4, wherein the pharmaceutical composition is administered by intracerebroventricular (ICV) delivery into the subject.

* * * * *

SEQUENCE LISTING

```
<160> NUMBER OF SEQ ID NOS: 5

<210> SEQ ID NO 1
<211> LENGTH: 114
<212> TYPE: DNA
<213> ORGANISM: Buthus martensi Karsch

<400> SEQUENCE: 1
tttggactca tagacgtaaa atgttttgca tctagtgaat gttggacagc ttgcaaaaaa     60
gtaacaggat cgggacaagg aaagtgccag aataatcaat gtcgatgcta ctga         114

<210> SEQ ID NO 2
<211> LENGTH: 37
<212> TYPE: PRT
<213> ORGANISM: Buthus martensi Karsch

<400> SEQUENCE: 2

Phe Gly Leu Ile Asp Val Lys Cys Phe Ala Ser Ser Glu Cys Trp Thr
1               5                   10                  15

Ala Cys Lys Lys Val Thr Gly Ser Gly Gln Gly Lys Cys Gln Asn Asn
            20                  25                  30

Gln Cys Arg Cys Tyr
        35

<210> SEQ ID NO 3
<211> LENGTH: 39
<212> TYPE: PRT
<213> ORGANISM: Artificial Sequence
<220> FEATURE:
<223> OTHER INFORMATION: Synthetic protein

<400> SEQUENCE: 3
```

Gly Ser Phe Gly Leu Ile Asp Val Lys Cys Phe Ala Ser Ser Glu Cys
1               5                   10                  15

Trp Thr Ala Cys Lys Lys Val Thr Gly Ser Gly Gln Gly Lys Cys Gln
            20                  25                  30

Asn Asn Gln Cys Arg Cys Tyr
            35

<210> SEQ ID NO 4
<211> LENGTH: 1254
<212> TYPE: DNA
<213> ORGANISM: Artificial Sequence
<220> FEATURE:
<223> OTHER INFORMATION: Synthetic nucleic acid

<400> SEQUENCE: 4

```
atgcatcatc atcatcatca tatgaaaatc gaagaaggta aactggtaat ctggattaac      60
ggcgataaag gctataacgg tctcgctgaa gtcggtaaga aattcgagaa agataccgga     120
attaaagtca ccgttgagca tccggataaa ctggaagaga aattcccaca ggttgcggca     180
actggcgatg ccctgacat tatcttctgg gcacacgacc gctttggtgg ctacgctcaa     240
tctggcctgt tggctgaaat caccccggac aaagcgttcc aggacaagct gtatccgttt     300
acctgggatg ccgtacgtta acggcaag ctgattgctt acccgatcgc tgttgaagcg     360
ttatcgctga tttataacaa agatctgctg ccgaacccgc aaaaacctg gaagagatc     420
ccggcgctgg ataagaact gaaagcgaaa ggtaagagcg cgctgatgtt caacctgcaa     480
gaaccgtact tcacctggcc gctgattgct gctgacgggg ttatgcgtt caagtatgaa     540
acggcaagt acgacattaa agacgtgggc gtggataacg ctggcgcgaa agcgggtctg     600
accttcctgg ttgacctgat taaaaacaaa cacatgaatg cagacaccga ttactccatc     660
gcagaagctg cctttaataa aggcgaaaca gcgatgacca tcaacggccc gtgggcatgg     720
tccaacatcg acaccagcaa agtgaattat ggtgtaacgg tactgccgac cttcaagggt     780
caaccatcca aaccgttcgt tggcgtgctg agcgcaggta ttaacgccgc cagtccgaac     840
aaagagctgg caaagagtt cctcgaaaac tatctgctga ctgatgaagg tctggaagcg     900
gttaataaag acaaaccgct gggtgccgta gcgctgaagt cttacgagga gagttggcg     960
aaagatccac gtattgccgc caccatggaa acgcccaga aggtgaaat catgccgaac    1020
atcccgcaga tgtccgcttt ctggtatgcc gtgcgtactg cggtgatcaa cgccgccagc    1080
ggtcgtcaga ctgtcgatga agccctgaaa gacgcgcaga ctctggtccc tagaggttct    1140
tttggactca tagacgtaaa atgttttgca tctagtgaat gttggacagc ttgcaaaaaa    1200
gtaacaggat cgggacaagg aaagtgccag aataatcaat gtcgatgcta ctga          1254
```

<210> SEQ ID NO 5
<211> LENGTH: 417
<212> TYPE: PRT
<213> ORGANISM: Artificial Sequence
<220> FEATURE:
<223> OTHER INFORMATION: Synthetic protein

<400> SEQUENCE: 5

Met His His His His His His Met Lys Ile Glu Glu Gly Lys Leu Val
1               5                   10                  15

Ile Trp Ile Asn Gly Asp Lys Gly Tyr Asn Gly Leu Ala Glu Val Gly
            20                  25                  30

Lys Lys Phe Glu Lys Asp Thr Gly Ile Lys Val Thr Val Glu His Pro

```
                35                  40                  45
Asp Lys Leu Glu Glu Lys Phe Pro Gln Val Ala Ala Thr Gly Asp Gly
         50                  55                  60

Pro Asp Ile Ile Phe Trp Ala His Asp Arg Phe Gly Gly Tyr Ala Gln
65                   70                  75                  80

Ser Gly Leu Leu Ala Glu Ile Thr Pro Asp Lys Ala Phe Gln Asp Lys
                 85                  90                  95

Leu Tyr Pro Phe Thr Trp Asp Ala Val Arg Tyr Asn Gly Lys Leu Ile
                100                 105                 110

Ala Tyr Pro Ile Ala Val Glu Ala Leu Ser Leu Ile Tyr Asn Lys Asp
             115                 120                 125

Leu Leu Pro Asn Pro Pro Lys Thr Trp Glu Glu Ile Pro Ala Leu Asp
         130                 135                 140

Lys Glu Leu Lys Ala Lys Gly Lys Ser Ala Leu Met Phe Asn Leu Gln
145                 150                 155                 160

Glu Pro Tyr Phe Thr Trp Pro Leu Ile Ala Ala Asp Gly Gly Tyr Ala
                165                 170                 175

Phe Lys Tyr Glu Asn Gly Lys Tyr Asp Ile Lys Asp Val Gly Val Asp
                180                 185                 190

Asn Ala Gly Ala Lys Ala Gly Leu Thr Phe Leu Val Asp Leu Ile Lys
             195                 200                 205

Asn Lys His Met Asn Ala Asp Thr Asp Tyr Ser Ile Ala Glu Ala Ala
         210                 215                 220

Phe Asn Lys Gly Glu Thr Ala Met Thr Ile Asn Gly Pro Trp Ala Trp
225                 230                 235                 240

Ser Asn Ile Asp Thr Ser Lys Val Asn Tyr Gly Val Thr Val Leu Pro
                245                 250                 255

Thr Phe Lys Gly Gln Pro Ser Lys Pro Phe Val Gly Val Leu Ser Ala
            260                 265                 270

Gly Ile Asn Ala Ala Ser Pro Asn Lys Glu Leu Ala Lys Glu Phe Leu
            275                 280                 285

Glu Asn Tyr Leu Leu Thr Asp Glu Gly Leu Glu Ala Val Asn Lys Asp
            290                 295                 300

Lys Pro Leu Gly Ala Val Ala Leu Lys Ser Tyr Glu Glu Glu Leu Ala
305                 310                 315                 320

Lys Asp Pro Arg Ile Ala Ala Thr Met Glu Asn Ala Gln Lys Gly Glu
                325                 330                 335

Ile Met Pro Asn Ile Pro Gln Met Ser Ala Phe Trp Tyr Ala Val Arg
                340                 345                 350

Thr Ala Val Ile Asn Ala Ala Ser Gly Arg Gln Thr Val Asp Glu Ala
            355                 360                 365

Leu Lys Asp Ala Gln Thr Leu Val Pro Arg Gly Ser Phe Gly Leu Ile
        370                 375                 380

Asp Val Lys Cys Phe Ala Ser Ser Glu Cys Trp Thr Ala Cys Lys Lys
385                 390                 395                 400

Val Thr Gly Ser Gly Gln Gly Lys Cys Gln Asn Asn Gln Cys Arg Cys
                405                 410                 415

Tyr
```